United States Patent [19]
Grant et al.

[11] Patent Number: 6,083,173
[45] Date of Patent: Jul. 4, 2000

[54] ARTIFICIAL NEURAL NETWORK FOR PREDICTING RESPIRATORY DISTURBANCES AND METHOD FOR DEVELOPING THE SAME

[75] Inventors: Brydon J. B. Grant, East Amherst; Ali El-Solh, West Seneca, both of N.Y.

[73] Assignee: Research Foundation of State University of New York, Amherst, N.Y.

[21] Appl. No.: 09/263,361

[22] Filed: Mar. 5, 1999

Related U.S. Application Data

[60] Provisional application No. 60/077,132, Mar. 6, 1998, and provisional application No. 60/077,148, Mar. 6, 1998.

[51] Int. Cl.[7] .............................. A61B 5/08; A61B 10/00; G06T 7/60

[52] U.S. Cl. ............................ 600/529; 128/924; 706/21; 706/924

[58] Field of Search .................................. 600/529, 300; 706/15, 21, 62, 924; 128/920, 924, 925

[56] References Cited

U.S. PATENT DOCUMENTS

| | | |
|---|---|---|
| 5,724,983 | 3/1998 | Selker et al. ............................. 600/509 |
| 5,839,438 | 11/1998 | Graettinger et al. ..................... 128/924 |

*Primary Examiner*—Cary O'Connor
*Assistant Examiner*—Navin Natnithithadha
*Attorney, Agent, or Firm*—Hodgson, Russ, Andrews, Woods & Goodyear LLP

[57] ABSTRACT

A method for predicting respiratory disturbances, and a method for developing such an artificial neural network. The inputs to the method and to the artificial neural network of the present invention are the answers given by a person to a series of questions. The output of the artificial neural network is a predicted respiratory disturbance index.

3 Claims, 7 Drawing Sheets

| | DERIVATION COHORT (N=189) | VALIDATION COHORT (N=80) |
|---|---|---|
| AGE±SD(YEARS) | 47.9+13.0 | 47.9+11.2 |
| GENDER(M:F) | 1.95:1 | 2.07:1 |
| BMI±SD(kg/m$^2$) | 35.4+9.2 | 34.4+9.0 |
| NC±SD(cm) | 41.6+5.8 | 41.9+5.2 |

FIG. 4

| | DERIVATION COHORT (N=189) | | VALIDATION COHORT (N=80) | |
|---|---|---|---|---|
| | SLEEP APNEA (N=131) | NO SLEEP APNEA (N=58) | SLEEP APNEA (N=51) | NO SLEEP APNEA (N=29) |
| AGE±SD(YEARS) | 48.6±12.2 | 47.1±14.9 | 47.6±11.1 | 48.3±11.4 |
| BMI±SD(kg/m$^2$) | 36.7±9.0 | 32.3±8.2* | 37.5±8.9 | 28.7±5.9* |
| NC±SD(cm) | 43.1±5.6 | 38.4±4.5* | 43.8±4.6 | 38.3±4.0* |
| AHI±SD | 61.3±40.6 | 4.1±3.0 | 52.5±33.4 | 4.0±3.3 |

(* INDICATES $P<0.01$ WHEN THOSE SUBJECTS WITH SLEEP APNEA ARE COMPARED TO THOSE WITH NO SLEEP APNEA)

CART VARIABLES

1. RESPONSE TO "I AM TOLD I STOP BREATHING IN MY SLEEP."
2. RESPONSE TO "I FEEL TIRED UPON AWAKENING AND WANT TO GO BACK TO SLEEP."
3. RESPONSE TO "MY DESIRE OR INTEREST IN SEX IS LESS THAN IT USED TO BE."
4. RESPONSE TO "AT NIGHT, MY SLEEP DISTURBS MY BED PARTNER'S SLEEP."
5. RESPONSE TO "I AM VERY SLEEPY DURING THE DAYTIME AND STRUGGLE TO STAY AWAKE."
6. RESPONSE TO "I HAVE OR HAVE BEEN TOLD THAT I HAVE RESTLESS LEGS."
7. BODY MASS INDEX.
8. NECK CIRCUMFERENCE.
9. AGE

LOGISTIC REGRESSION VARIABLES

1. RESPONSE TO "I AM TOLD I STOP BREATHING IN MY SLEEP."
2. RESPONSE TO "I SUDDENLY AWAKE GASPING FOR BREATH DURING THE NIGHT."
3. RESPONSE TO "I AM TOLD I SNORE IN MY SLEEP."
4. RESPONSE TO "DO YOU HAVE OR ARE YOU BEING TREATED FOR HIGH BLOOD PRESSURE?"
5. BODY MASS INDEX.
6. NECK CIRCUMFERENCE.

VARIABLES NOT SELECTED

1. RESPONSE TO "FALLING ASLEEP WHILE ENGAGED IN AN ACTIVITY."
2. RESPONSE TO "FALLING ASLEEP WHILE IN A QUIET, PASSIVE, OR RELAXING SITUATION."
3. RESPONSE TO "I HAVE HAD ACCIDENTS OR NEAR ACCIDENTS WHILE OPERATING A MOTOR VEHICLE."
4. RESPONSE TO "I HAVE DIFFICULTY FALLING ASLEEP."
5. RESPONSE TO "WHEN I AWAKEN DURING THE NIGHT, I HAVE DIFFICULTY FALLING BACK TO SLEEP."
6. GENDER
7. AMOUNT OF ALCOHOL INGESTION.

ARTIFICIAL NEURAL NETWORK FOR PREDICTING RESPIRATORY DISTURBANCES AND METHOD FOR DEVELOPING THE SAME

CROSS-REFERENCE TO RELATED APPLICATIONS

This application claims priority to two earlier filed U.S. provisional patent applications, U.S. provisional patent application Ser. No. 60/077,132, which was filed on Mar. 6, 1998, and U.S. provisional patent application Ser. No. 60/077,148, which filed on Mar. 6, 1998, both of which are incorporated herein by reference.

FIELD OF THE INVENTION

The present invention relates to an artificial neural network ("ANN") for predicting respiratory disturbances, and a to method for developing such an ("ANN").

BACKGROUND ART

Regression models have been used to produce prediction rules for predicting whether an individual has a particular attribute, such as a sleeping disorder. Such regression models often use physical features and clinical traits indicative of a high probability of the attribute. However, the predictive rules produced by such regression models often lack specificity, and offer only a dichotomous output based on a predetermined cutoff value, particularly with respect to the apnea/hypopnea index ("AHI"), which is an index related to obstructive sleep apnea ("OSA"). Furthermore, to compound the deficiencies of such prediction rules, the predetermined cutoff value associated with a particular model is often selected arbitrarily, and furthermore, varies from model to model. Moreover, the statistical methods used to derive these models may not fully take into account non-linear attributes of complex processes.

OSA has been recognized increasingly as an important public health problem with potentially serious cardiovascular and psychomotor morbidity, and possibly excessive mortality. An increased awareness of the risks associated with OSA in recent years has led to an increase in the number of referrals to specialists and sleep laboratories. Overnight polysomnography ("OPG") is the standard reference test for diagnosing OSA. However, OPG is an expensive, labor-intensive, and time consuming procedure. As a result, there is a need for a practical and less work-intensive screening test to allow physicians to estimate whether patients have OSA.

SUMMARY OF THE INVENTION

The present invention provides an ANN for predicting respiratory disturbances, and a method for developing an ANN.

An object of the present invention is to provide a method of developing an ANN which results in a prediction having more specificity and having fewer dichotomous outputs than prior art prediction rules developed through regression analysis models.

Furthermore, it is an object of the present invention to take into account nonlinear relationships and intricate inter-relationships among attributes of complex processes, such as a biological system.

Another object of the present invention is to provide a screening test for predicting OSA which is less expensive to use, less labor-intensive to use, and less time consuming to use than OPG.

DETAILED DESCRIPTION OF THE PREFERRED EMBODIMENT

Figure 1:
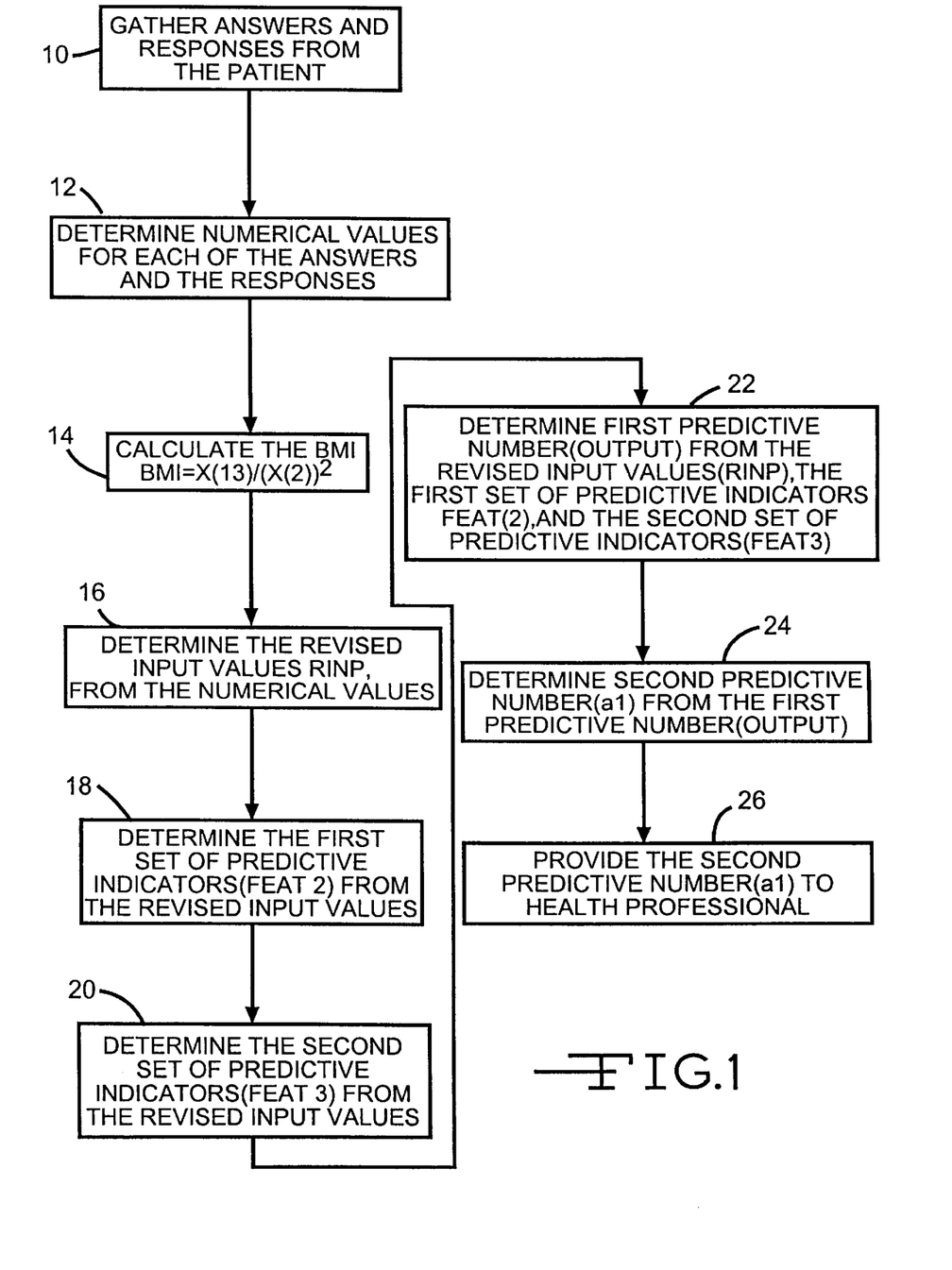
FIG. 1 shows the steps of the ANN according to the present invention.

The present invention includes a method, referred to herein generally as an ANN, that can predict the AHI of patients suspected of OSA. The ANN of the present invention uses a combination of anthropomorphic data and clinical information obtained from a patient to predict the AHI of that patient. The AHI is indicative of the likelihood that an individual has OSA. FIG. 1 shows the method steps of the present invention. The present invention is also directed at a storage device, such as a floppy disk, having stored thereon computer readable code for causing a computer to execute all or a substantial portion of the ANN.

Figure 2:
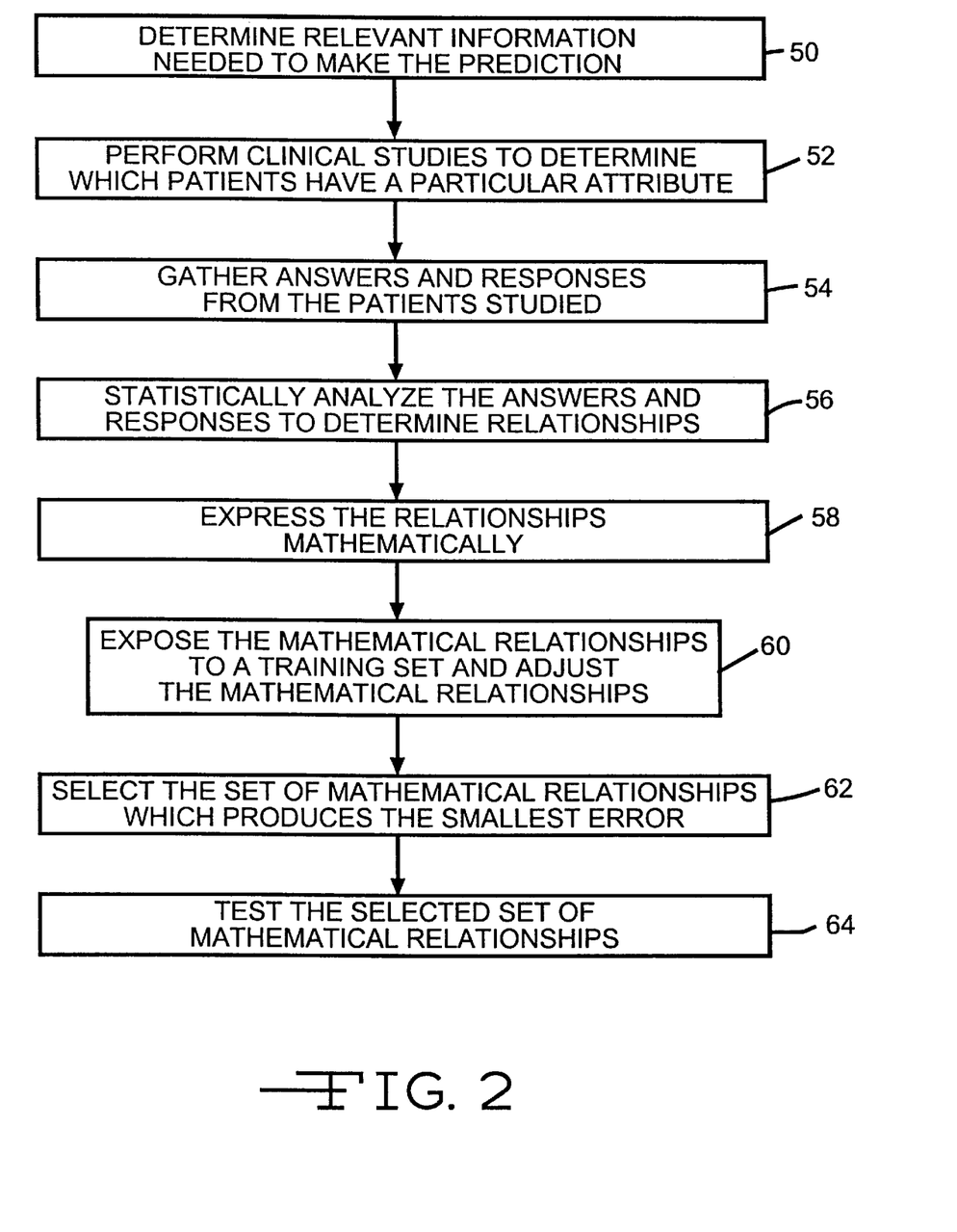
FIG. 2 shows the steps of the method for developing an ANN according to the present invention.

Furthermore, the present invention includes a method for developing an ANN, such as the ANN described herein. FIG. 2 shows the method steps of this aspect of the present invention. An ANN is a numerical processor that accepts multiple pieces of information, usually in digital form, performs calculations using the pieces of information, and produces results which state whether an attribute is likely to be present. In an embodiment of the present invention, described below in more detail, the pieces of information gathered as part of the method are answers given by a patient in response to certain questions and statements, and the result produced by the ANN is a predicted AHI.

In an embodiment of the present invention, the method begins (step 10) by gathering information in the form of answers and responses to questions and statements. In the present invention, the information includes answers given by the patient to the following questions: (a) How old are you (in years)?, (b) How tall are you (in meters)?, (c) How much do you weigh (in kilograms)?, (d) What is your neck circumference (in centimeters)?, (e) Have you been told or been treated for high blood pressure? (if yes, enter "1", and if no, enter "0"). The information gathered (step 10) from the patient also includes the responses given by the patient to a set of statements. For ease in gathering the information, the patient is permitted to give one of five possible responses for each statement in the set of statements. Furthermore, each possible response is associated with a number (step 12). The number is determined and used in subsequent steps of the method according to the present invention in lieu of the response itself. In an embodiment of the present invention, the possible responses to each statement in the set of statements, and the number associated with each possible response are as follows: a response of "0.5" means not sure, do not know or is not applicable, a response of "0" means strongly disagree or never, a response of "0.25" means disagree or rarely has occurred, but less than once per week, a response of "0.5" means somewhat agree or sometimes i.e. 1 to 2 times per week, a response of "0.75" means agree or frequently i.e. 3 to 4 times per week, and finally, a response of "1.0" means strongly agree or always or almost always i.e. 5 to 7 time per week. The set of statements includes the following: (a) I am very sleepy during the daytime and struggle to stay awake, (b) At night, my sleep disturbs my bed partner's sleep, (c) I am told I snore in my sleep, (d) I am told I stop breathing in my sleep, (e) I suddenly wake up gasping for breath during the night, (f) I feel tired upon awakening and want to go back to sleep, (g) I have or have been told that I have restless legs, (h) My desire or interest in sex is less than it used to be.

In Appendix A, incorporated herein by reference, there is shown the source code for a computer program called "sleep.prg" which will cause a computer to prompt the user of such a computer for responses to the questions and statements discussed above. A computer having sleep.prg running thereon expedites the step of gathering (step 10) the answers and responses from the patient. Sleep.prg is shown in Appendix A written in Clipper, but other computer languages can be used to gather the answers to the questions and responses to the statements discussed above. As shown in Appendix A, sleep.prg accepts measurements in the English or metric system, and may convert entries to a different measurement system. In addition, sleep.prg accepts responses to each statement in the set of statements in the form of a number 1 through 5, but then converts each response entered by the user into a number 0 through 1, as discussed above. Finally, sleep.prg puts the answers and responses in a string so that such information can be quickly accepted and processed by means for executing subsequent steps of the method, discussed below.

Appendix B, incorporated herein by reference, is the source code for a computer program called "sleepnet.for" which executes subsequent steps of the ANN according to the present invention. Sleepnet.for is shown in Appendix B written in Fortran, but other computer languages can be used to cause a computer to execute the steps according to the ANN. As shown in Appendix B, sleepnet.for is written to accept the answers and responses discussed above in the format produced by sleep.prg.

For ease of reference, X(1) through X(13) will be used herein to indicate the numerical values associated with the answers and responses (described above) given by a patient. X(1) relates to the patient's age, X(2) relates to the patient's height, X(3) relates to the patient's neck circumference, and X(4) relates to the patient's blood pressure, and X(5) relates to whether the patient is sleepy during the daytime. X(6) relates to whether the patient disturbs the bed partner, X(7) relates to whether the patient snores, X(8) relates to whether the patient stops breathing while sleeping, and X(9) relates to whether the patient suddenly wakes up gasping for breath. X(10) relates to whether the patient is tired upon awakening, X(11) relates to whether the patient has restless legs, X(12) relates to the patient's desire to have sex, and X(13) relates to the patient's weight.

In the next step 14 of the ANN according to the present invention, a BMI value is determined. The BMI value is determined by dividing X(13) by the square of X(2). In a subsequent step 16 of the ANN, twelve revised input values, herein referred to as RINP(1) through RINP(12), are determined as indicated in Appendix B from the numerical values X(1) through X(13). RINP(1) relates to age, RINP(2) relates to the BMI calculated, RINP(3) relates to neck circumference, RINP(4) relates to blood pressure, RINP(5) relates to being sleepy during the daytime. RINP(6) relates to disturbing the bed partner, RINP(7) relates to snoring, RINP(8) relates to stopping breathing while sleeping, and RINP(9) relates to suddenly waking up gasping for breath. RINP(10) relates to being tired upon awakening, RINP(11) relates to restless legs, and RINP(12) relates to desire to have sex.

In the next step 18, a first set of predictive indicators, the components of which are referred to herein as "feat2", is determined. Feat2 includes twenty-one (21) predictive indicators shown in Appendix B as feat2(1) through feat2(21), and are determined as shown in Appendix B from the revised input values RINP(1) through RINP(12). In a next step 20, a second set of predictive indicators, the components of which are referred to herein as "feat3", is determined. Feat3 includes twenty-one (21) predictive indicators shown in Appendix B as feat3(1) through feat3(21), and are determined as shown in Appendix B from the revised input values RINP(1) through RINP(12).

In the next step 22 of the ANN according to the present invention, RINP(1) through RINP(12) are combined with the first and second sets of predictive indicators as shown in Appendix B to produce a first predictive number, labeled "output" in Appendix B. As shown in Appendix B, the first predictive number ("output") is a number between 10 and −10. The calculations shown in Appendix B may be adjusted to provide for AHI thresholds different from 10 per hour, and the present invention is not limited to the first predictive number ("output") being between 10 and −10. In the next step 24 of the method, a second predictive number, labeled "a1" in Appendix B, is determined as shown in Appendix B. The second predictive number, a1, once manipulated according to Appendix B, is the predicted AHI and in the final step 26, is provided to a health professional, such as a physician.

The present invention also includes a method for developing an ANN, such as the ANN described above. The method for developing an ANN is described by way of the example which follows and in FIG. 2. Furthermore, the ANN described above is further described and explained by the example which follows.

In a first step 50 of the method for developing an ANN, relevant information which is needed to make the desired prediction is determined. In a next step 52 of the method for developing an ANN, clinical studies are performed to determine which patients have a particular attribute. As an example of this step 52, patients were referred to the Sleep Center at Buffalo General Hospital between November 1995 and August 1996 and were identified retrospectively from the sleep registration records and represented the derivation cohort. The majority of patients were referred by internists (54%), internal medicine subspecialists (36%), or ear, nose and throat surgeons (7%). In this example, sleep studies (OPG) were performed on two hundred ninety three patients during this period. Patients were excluded if they had been previously treated for sleep apnea, referred for a specific sleep disorder other than sleep apnea, or they failed to complete the sleep study.

In the next step 54 of the method, patients give answers to questions and respond to statements and these answers and statements are gathered for further analysis. In the present example a questionnaire related to sleep symptoms and motor functions was filled out by all patients prior to undergoing OPG. Demographic information (age, gender) and anthropomorphic measurements (neck circumference, height, and weight) were obtained on each patient.

The questionnaire administered to each patient sought answers and responses about a range of clinical variables thought to contribute or raise suspicion of sleep apnea. Nineteen (19) questions were subjected to detailed analysis. The questions had a six-item Likert response with the following options: never (or strongly disagree), rarely (or disagree), sometimes (or somewhat agree), frequently (somewhat agree), always (strongly agree), and not sure (or not applicable). In addition, the presence of hypertension and the amount of alcohol ingestion were determined by patient's self report.

OPG was conducted on all patients enrolled in the study at the Sleep Center. Continuous electroencephalogram, electroculogram, electrocardiogram, and submental electromyogram were recorded. Airflow was assessed with an oral and nasal thermistor (Graphic Control; Buffalo, N.Y.), and arterial oxyhemoglobin saturation was measured with a pulse oximeter with the probe placed on the patient's finger (Biox IIA or 3700, Ohmeda; Louisville, Colo.). Abdominal wall and rib cage motions were recorded with an inductive plethysmograph (Respitrace Corporation; Ardsley, N.Y.). AH data were recorded on a 16-channel polygraph and digitized on a computerized system (Aekitron Medical; Minneapolis, Minn.).

Sleep stages were scored in 30-sec epochs using the Rechtschaffen and Kales sleep scoring criteria. Each epoch was analyzed for the number of apneas, hypopneas, arousals, oxyhemoglobin desaturation, and disturbances in cardiac rate and rhythm. Apnea was defined as a reduction in airflow of >80% at the nose and the mouth for at least 10 sec. Hypopnea was defined as a 50% reduction in oronasal airflow associated with either a 4% or greater decrease in oxygen saturation, or an arousal. Arousal was defined according to the recent ASDA position paper (ASDA Report, EEG arousals: scoring rules and examples, Sleep 1992; 15:173–5). The record was scored manually by a polysomnography technician and reviewed by a physician certified in sleep medicine. The number of apneas and hypopneas per hour of total sleep time was derived, and reported as the apnea-hypopnea index (AHI). A positive sleep study for sleep apnea was defined as a AHI>10/hour, other thresholds were also considered (>15 or >20/hour) to determine the effect of altering the definition on the diagnostic accuracy of the predictive models.

In the next step 56 of the method, the answers and responses are statistically analyzed to determine relationships between the answers and responses and the results of the clinical studies for the patients. In the present example, descriptive statistics for continuous variables were expressed as mean ±1 SD (standard deviation). Difference in mean values was assessed using Student's t test. All tests were two tailed and statistical significance was set at a p value of less than 0.05. Commercially available software were used for the multiple linear regression and regression tree (S-Plus, Statsci, Seattle, Wash. ), artificial neural networks (Neuroshell 2, Ward Systems, Frederick, Md.), and for confidence interval analyses (CIA, British Medical Journal, London, UK). A logarithmic transformation of AHI was used for both the ANN and the multiple linear regression in order to achieve a normal distribution of residuals.

The variables used as inputs for the ANN were selected from the list of items obtained from the patient's questionnaire and from anthropomorphic measurements. The classification and regression tree was used to choose those variables more likely to influence the predictive properties of the ANN. Because logistic regression models sometimes perform better than a decision tree, a logistic regression was also performed to identify predictor variables. The independent variables were scaled to a value over a range between −1 and 1. The responses to the Likert scale values were spaced equally at intervals of 0.5 over this range. Missing values and responses marked as "not applicable" were substituted with the class mean.

In the next step 58 of the method, the relationships determined in the prior step are expressed mathematically. The ANN described in this study was based on three layers: an input layer with 12 nodes, an output layer with a linear function and a hidden layer. The hidden layer consisted of a direct connection between the input and the output layers, and two groups of 21 nodes with differing activation functions. The activation function describes the nature of the linkage between the input layer and the hidden layer. A Gaussian function was used for one group and a hyperboric function (tanh) for the other. Connections and outputs from the two groups in the hidden layer were linked to the output layer by linear functions. Each link was assigned a coefficient or weights that was updated during the learning process. The weights are assigned initially at random between −0.6 and +0.6.

In the next step 60, the mathematically expressed relationships are exposed to a training set during which the mathematical relationships are presented with a set of input and output patterns. During this training phase, the inputs are fed into the mathematical relationships and the corresponding outcome is computed. The difference between the actual and desired outcome is propagated backward. Adjustments to connection weights in the mathematical relationships are made to minimize the error between the output predicted by the mathematical relationships and the measured attribute, in this example, the AHI. During training, the mathematical relationships are tested at regular intervals to determine the prediction error on a subset of data (evaluation data set) that is not included in the training process. As training proceeds, the prediction error on the evaluation data set decreases initially but then increases when overtraining occurs. The mathematical relationships that produce the smallest error are selected (step 62)for further analysis.

In the present example, a tenfold cross validation approach was used for evaluation. The entire data set of 189 patients was divided with a random number generator into ten subsets. Nine out of the ten subsets was pooled and used for training. The data from the tenth subset was used as an evaluation set during training. The entire process was repeated nine additional times by rotating the subset that was used as the evaluation set during training. The mean square error was computed for each of ten sets of mathematical relationships on the entire derivation data set. The mean square errors were averaged and the set of mathematical relationships that had a mean square error closest to the average was selected.

A multiple linear regression was employed to develop a model of AHI score based on the same independent variables used in the chosen set of mathematical relationships. Interaction terms were not included to determine the extent to which non-linearities and interaction terms contributed to the predictive accuracy of the chosen set of mathematical relationships.

In the next step 64 of the method, the predictive model embodied by the chosen set of mathematical relationships is tested on an entirely different set of patients (validation cohort) that were not included in the derivation set. The validation cohort used to develop the above described ANN comprised all patients who underwent a sleep study between September 1996 and December 1996. Patients were excluded from the study if they had been previously treated for sleep apnea, referred for a specific sleep disorder other than sleep apnea, or they failed to complete the sleep study.

Then, a receiver operator characteristic (ROC) curve was generated for the chosen set of mathematical relationships. The ROC curve represents a graphic display of the true positives (sensitivity) plotted against the false positives (1-specificity) for various thresholds that are used to define sleep apnea. The c-index was used to estimate diagnostic accuracy. The c-index is equivalent to the area under the ROC curve. In brief, it is calculated by determining the probability of diagnosing sleep apnea correctly in every possible pair of patients: one who has sleep apnea, the other who does not. A bootstrap method was used to calculate directly this measure of accuracy by generating 1000 data sets from a database by random sampling with replacement. Comparisons between the c-index for both models were assessed based on the confidence intervals. Statistical significance was accepted at the 5% level.

To determine the predictive performance of the ANN, the relation between the actual and predictive values of the AHI were compared by linear regression. The point wise 95% confidence limits of that linear regression were used to establish the confidence interval of the predicted AHI. Comparison between the predictive accuracy of the ANN and multiple linear regression was made with correlation coefficients. The actual values of AHI were correlated with the predicted values. The correlation coefficient for the ANN was compared with the correlation coefficient obtained by multiple linear regression.

Figure 3:
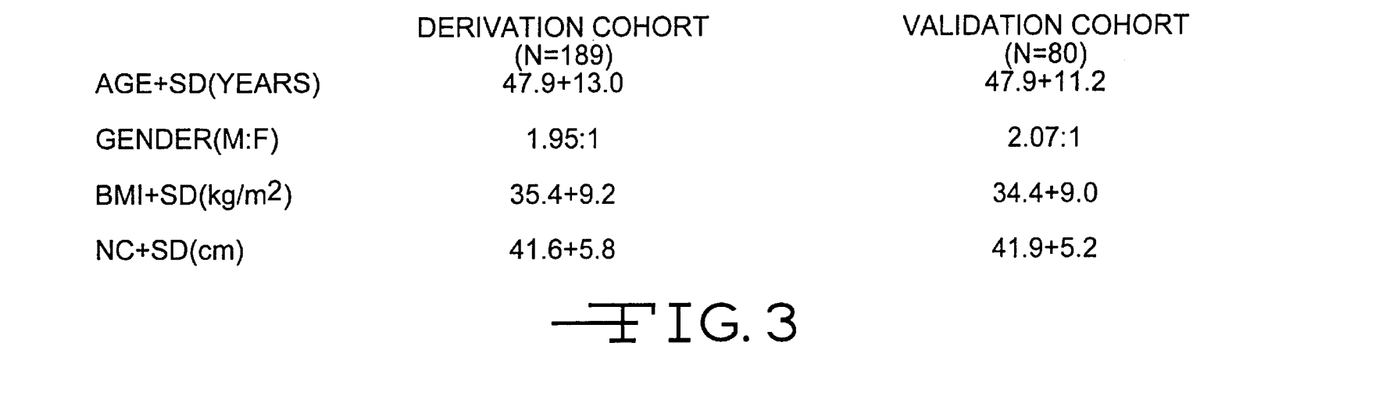
FIG. 3 shows demographics of a validation data set described herein.

The results of the above described method and the predictive ability of the ANN are described below, and the description which follows further illustrates the methods described above. Between November 1995 and December 1996, 289 sleep studies were performed at the Sleep Center. Twenty were excluded from further analysis: 12 patents were already diagnosed with sleep apnea, 6 patients were referred for a evaluation of sleep disorder other than sleep apnea, and 2 patients did not complete the sleep study. The derivation cohort was comprised of 189 patients, 66% males and 34% females. There were no significant differences in age, gender ratio, body mass index or neck circumference of patients of the derivation data set compared with the validation data set as, shown in FIG. 3.

Figure 4:
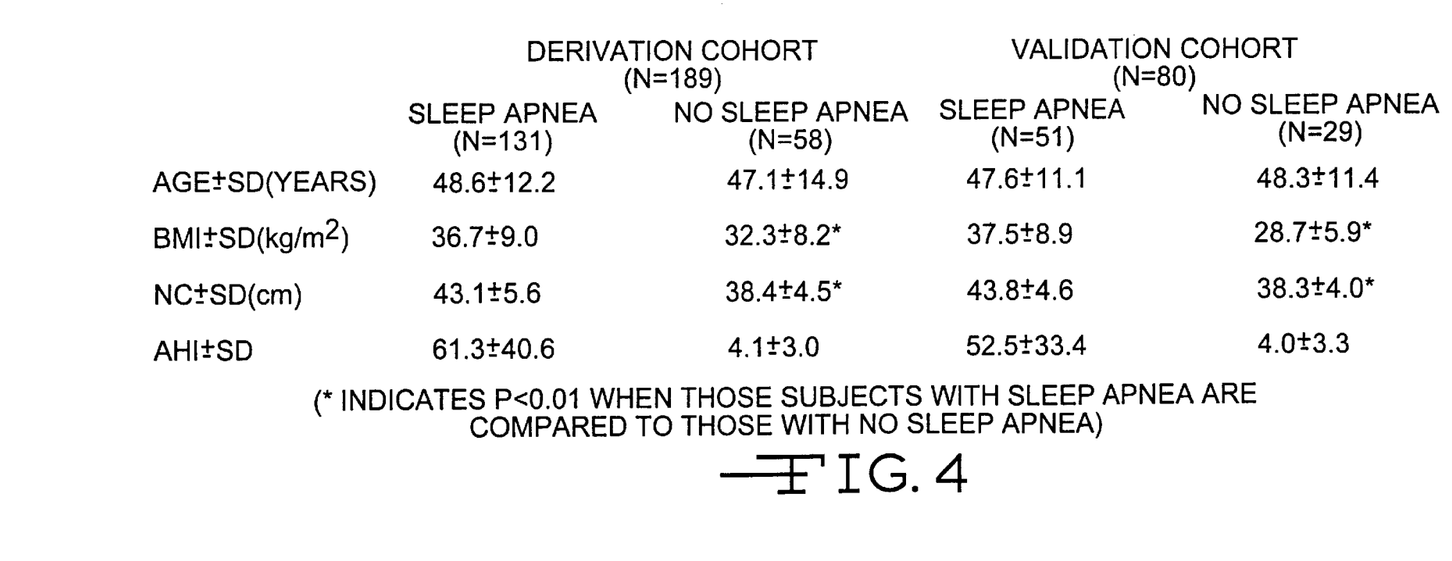
FIG. 4 is a comparison between patients who participated in a sleep study described herein.

Even accounting for the greater number of men than women in the cohort, there was a predominance of sleep apnea among males (Chi-square Yates corrected p=0.022). The age ranged from 14 to 95 years with a mean of 48.1 ±12.1 for those with sleep apnea, and 47.0 ±14.8 for those without sleep apnea (p=0.2), shown in FIG. 3. Fifty eight (31%) were found to be non-apneic (AHI 0–10), 23 (12%) to have mild obstructive sleep apnea (AHI 11–20), 28 (15%) to have moderate sleep apnea (AHI 21-40), and 80 (42%) to have severe sleep apnea (AHI>40). Patients with sleep apnea were significantly more obese (p<0.01) and had a larger neck circumference (p<0.01) than their non-apneic counterparts (see FIG. 4). The validation cohort consisted of 80 patients; 54 males (68%) and 26 (32%) females. Eighty one percent of respondents had no missing data. The number of respondents missing one, two, three, or four apnea symptoms items were 32 (13%), 12 (6%), 2 (0.7%), and 1 (0.3%) respectively.

Figure 5:
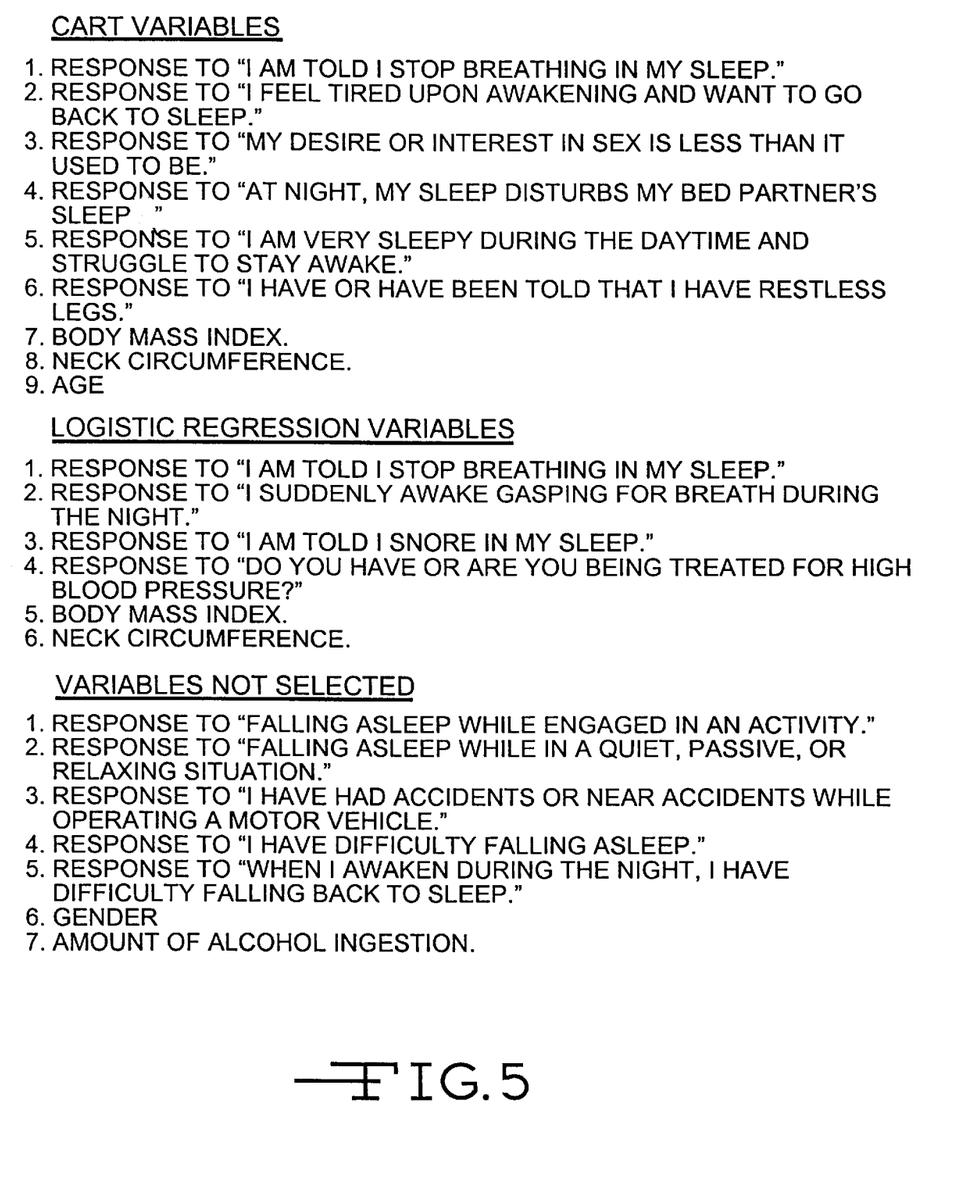
FIG. 5 is a list of questions and statements used to develop the ANN of the present invention.

Nine of 19 independent variables were selected in the final construction of the classification and regression tree. Six of the 19 independent variables of the logistic regression had coefficients that were statistically significant. Three of the six were not present in the classification and regression tree. Therefore, 12 variables were used as inputs to the ANN: nine from the classification and regression tree, and three additional variables from the logistic regression analysis. The questions to which responses were deemed to have significant predictive power for sleep apnea by the classification and regression tree and by logistic regression analysis are listed in FIG. 5. Body mass index, neck circumference, and episodes of apneic events during sleep were the only parameters common to both analyses.

The average of the mean square error of the ten ANNs performed was 0.089 (range 0.174–0.023). The ANN selected and described above had a mean square error of 0.092. The correlation coefficient from the ANN's predicted values of AHI and the actual values in the derivation set was 0.856. The corresponding correlation coefficient for the multiple linear regression with the same predictor variables was 0.509. This value was significantly less than the correlation coefficient obtained with the ANN (p<0.01).

Figure 6:
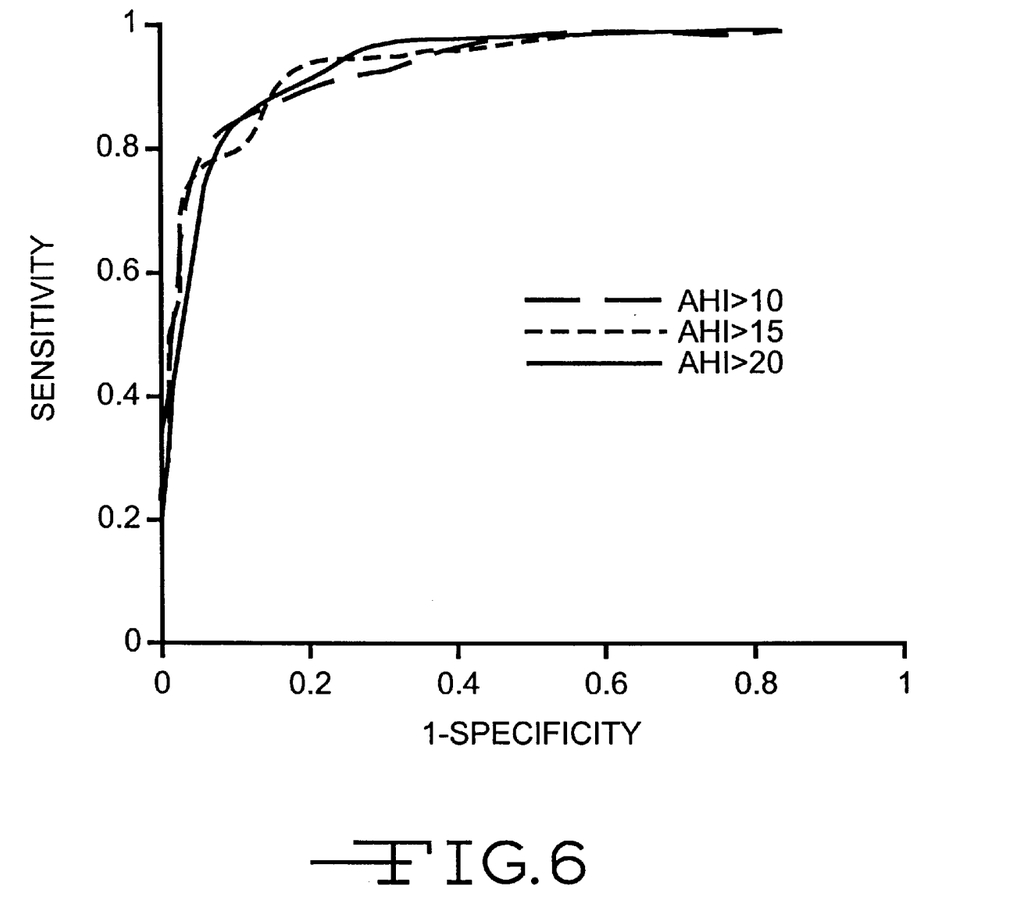
FIG. 6 is a graph showing receiver operator characteristic curves used to develop and analyze the ANN of the present invention.
Figure 7:
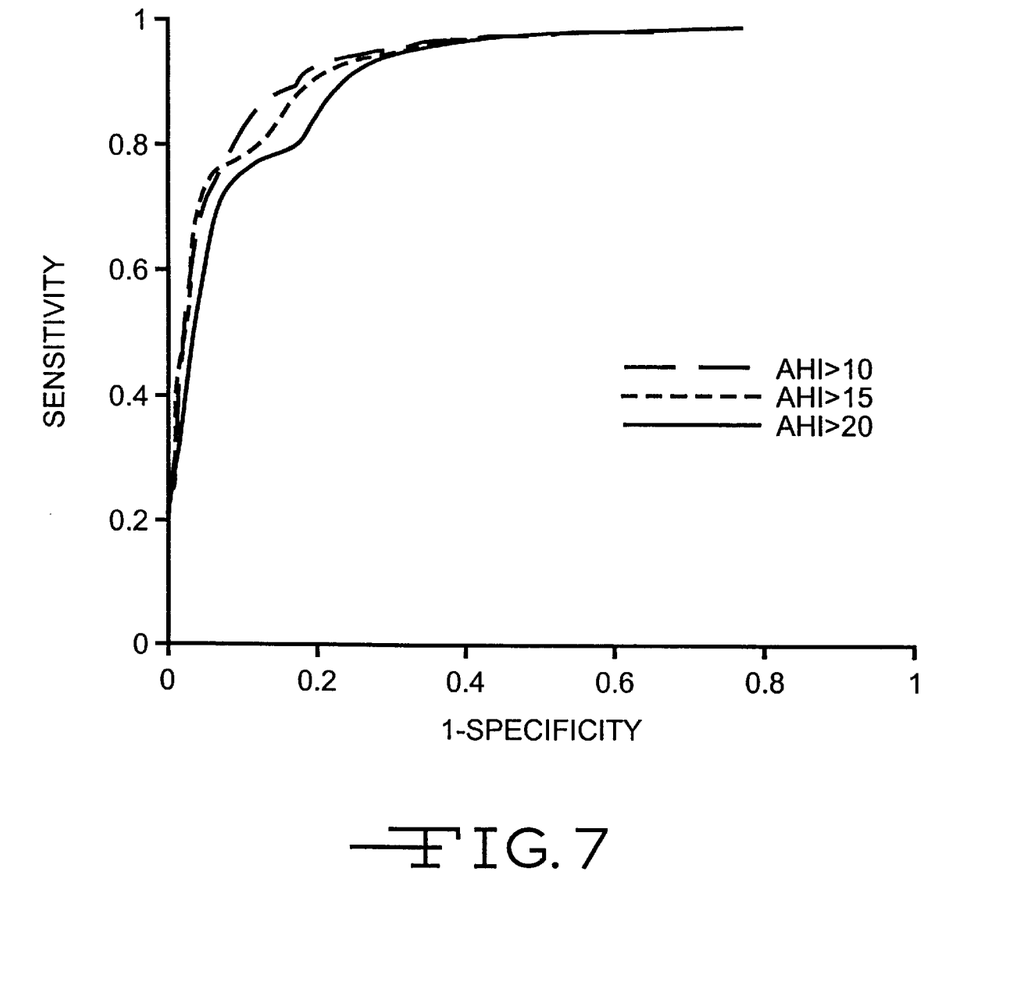
FIG. 7 is another graph showing receiver operator characteristic curves used to develop and analyze the ANN of the present invention.

The performance of the ANN using a dichotomous definition of OSA is shown in FIG. 6 for the derivation data set as ROC curves. The c-index which is equivalent to the area under the ROC curve, was 0.946 ±0.0151 SE, 0.948 ±0.0149 SE, and 0.944 ±0.0159 SE when OSA is defined as an AHI of >10, >15 and >20/hour respectively. There were no statistically significant differences between these c-indices. Similarly, the performance of the ANN using a dichotomous definition of OSA is shown in FIG. 7 for the validation data set as ROC curves. The c-index was 0.96 ±0.0191 SE, 0.951 ±0.0203 SE, and 0.935 ±0.0274 SE when OSA is defined as an AHI of >10, >15 and >20/hour respectively. There were no statistically significant differences between these c-indices or with the corresponding c-indices obtained with the derivation data set.

Figure 8:
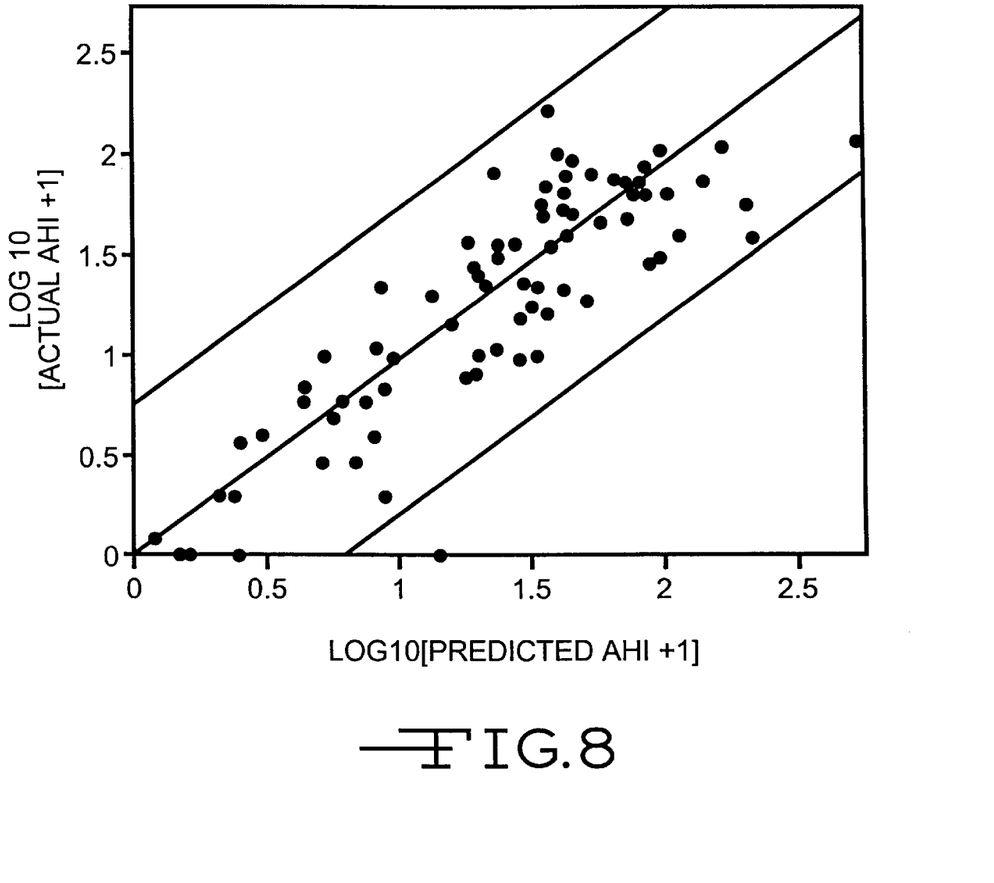
FIG. 8 shows the relation between the predicted and actual AHI for patients in the validation data set together with the point wise 95% confidence limits.

FIG. 8 shows the relation between the predicted and actual values of AHI for the patients in the validation data set together with the point wise 95% confidence limits. Only one of the 80 values (1.25% 95% CI:0–6.7%) fell outside of the 95% confidence limits.

As will be recognized by one skilled in the art, the present invention is a method, in the form of an ANN, which takes into account nonlinear relationships and intricate interrelationships among attributes of a complex process. The present inventions also presents a method for developing an ANN which results in a prediction having more specificity and fewer dichotomous outputs than prior art prediction rules developed through regression analysis modes. It is therefore apparent that the present invention accomplishes the intended objects described above. Although embodiments of the present invention have been described in detail herein, the present invention is not limited to such embodiments and is limited by the appended claims.

What is claimed is:

1. A method for predicting respiratory disturbances comprising:

gathering information from a patient, the information comprising pieces of information answers to questions and responses to statements;

determining numerical values for each of the answers and responses;

determining a first set of predictive indicators from the pieces of information;

determining a second set of predictive indicators from the pieces of information;

determining a predictive number from the pieces of information, the first set of predictive indicators, and the second set of predictive indicators, wherein the predictive number corresponds to a respiratory disturbance index; and providing the predictive number to a health professional.

2. A storage device having stored thereon computer readable code for causing a computer to execute the method of claim 1.

3. A method for developing an artificial neural network for making a prediction about an attribute comprising:

determining relevant information needed to make a prediction;

performing clinical studies on patients to determine which patients have a particular attribute and to produce results corresponding to the attribute;

gathering information about the patients, the information comprising pieces of information;

statistically analyzing the information gathered to determine relationships between the pieces of information and the results from the clinical studies;

expressing the relationships mathematically;

exposing the mathematical relationships to a training set and adjusting the mathematical relationships to produce a desired outcome; and testing the adjusted mathematical relationships.

* * * * *